US011911365B2

(12) United States Patent
Alpert

(10) Patent No.: US 11,911,365 B2
(45) Date of Patent: *Feb. 27, 2024

(54) COMPOSITION COMPRISING A DIINDOLYLMETHANE AND A RETINOID TO TREAT A SKIN CONDITION

(71) Applicant: SKINTECH LIFE SCIENCE LIMITED, Hertfordshire (GB)

(72) Inventor: David Alpert, London (GB)

(73) Assignee: SKINTECH LIFE SCIENCE LIMITED, Hertfordshire (GB)

( * ) Notice: Subject to any disclaimer, the term of this patent is extended or adjusted under 35 U.S.C. 154(b) by 193 days.

This patent is subject to a terminal disclaimer.

(21) Appl. No.: 17/195,535

(22) Filed: Mar. 8, 2021

(65) Prior Publication Data

US 2021/0260028 A1 Aug. 26, 2021

Related U.S. Application Data

(63) Continuation of application No. 16/684,300, filed on Nov. 14, 2019, now Pat. No. 10,966,958, which is a continuation of application No. 15/881,453, filed on Jan. 26, 2018, now Pat. No. 10,500,189, which is a continuation of application No. 15/137,481, filed on Apr. 25, 2016, now Pat. No. 9,907,785, which is a continuation of application No. 14/864,632, filed on Sep. 24, 2015, now Pat. No. 9,351,958, which is a continuation of application No. 14/007,247, filed as application No. PCT/EP2012/055032 on Mar. 21, 2012, now Pat. No. 9,180,117.

(30) Foreign Application Priority Data

Mar. 25, 2011 (GB) .................................. 1105050

(51) Int. Cl.
| | | |
|---|---|---|
| A61K 31/215 | (2006.01) | |
| A61K 31/404 | (2006.01) | |
| A61K 31/07 | (2006.01) | |
| A61K 31/203 | (2006.01) | |
| A61K 31/216 | (2006.01) | |
| A61K 45/06 | (2006.01) | |
| A61K 9/00 | (2006.01) | |
| A61K 31/341 | (2006.01) | |
| A61K 31/566 | (2006.01) | |
| A61K 31/22 | (2006.01) | |
| A61K 31/23 | (2006.01) | |

(52) U.S. Cl.
CPC .......... *A61K 31/404* (2013.01); *A61K 9/0014* (2013.01); *A61K 9/0053* (2013.01); *A61K 31/07* (2013.01); *A61K 31/203* (2013.01); *A61K 31/215* (2013.01); *A61K 31/216* (2013.01); *A61K 31/22* (2013.01); *A61K 31/23* (2013.01); *A61K 31/341* (2013.01); *A61K 31/566* (2013.01); *A61K 45/06* (2013.01)

(58) Field of Classification Search
CPC .................................................... A61K 31/215
See application file for complete search history.

(56) References Cited

U.S. PATENT DOCUMENTS

| | | | |
|---|---|---|---|
| 5,962,517 A | 10/1999 | Murad | |
| 9,180,117 B2* | 11/2015 | Alpert | .................. A61K 31/215 |
| 9,351,958 B2* | 5/2016 | Alpert | .................... A61K 31/07 |
| 9,907,785 B2* | 3/2018 | Alpert | .................... A61K 31/22 |
| 10,500,189 B2* | 12/2019 | Alpert | .................. A61K 9/0014 |
| 10,966,958 B2* | 4/2021 | Alpert | ..................... A61P 17/08 |
| 2005/0058600 A1 | 3/2005 | Bjeldanes et al. | |
| 2009/0035369 A1 | 2/2009 | Sela | |
| 2010/0029765 A1 | 2/2010 | Gupta et al. | |
| 2010/0055201 A1 | 3/2010 | Zeligs | |
| 2016/0367528 A1 | 12/2016 | Alpert | |

FOREIGN PATENT DOCUMENTS

| | | | |
|---|---|---|---|
| CA | 2797558 | C | 12/2014 |
| CN | 1463636 | A | 12/2003 |
| CN | 101428016 | A | 5/2009 |
| CN | 101884642 | A | 11/2010 |
| JP | H03500767 | A | 2/1991 |
| JP | 2008137936 | A | 6/2008 |
| JP | 2008174557 | A | 7/2008 |
| JP | 6132360 | B2 | 5/2017 |
| WO | 8809788 | A1 | 12/1988 |
| WO | 03034992 | A2 | 5/2003 |
| WO | 2005089412 | A2 | 9/2005 |
| WO | 2006047716 | A2 | 5/2006 |
| WO | 2006083458 | A2 | 8/2006 |
| WO | 2007096886 | A2 | 8/2007 |
| WO | 2009103754 | A2 | 8/2009 |

(Continued)

OTHER PUBLICATIONS

JP Office Action for related application No. 2019-220640 dated Jun. 14, 2021, 2 pages.
Johnson, Merck manual online, Vitamin A, <http:merckmanual.jp/mmpej/sec01/choo4/ch004h.html#>, 2007, 2 pages, Japanese only.
Kim et al. 3,3'-diindolylmethane suppresses 12-0-tetradecanoylphorbol-13-acetate-induced inflammation and tumor in mouse skin. Molecular Carcinogenesis 49(7):672-683 (2010).
May's Chemistry of Synthetic Drugs, pp. 12-19 (1964).
Nankodo, Today's therapeutic medication, pp. 388, 389, 896 http://www.nankodo.com.jp (2003) 3 pages, Japanese only.
PCT/EP2012/055032 International Search Report and Written Opinion dated May 18, 2012, 8 pages.

(Continued)

*Primary Examiner* — Rei Tsang Shiao
(74) *Attorney, Agent, or Firm* — PROCOPIO, CORY, HARGREAVES & SAVITCH LLP

(57) ABSTRACT

Provided is a composition for use in treating a skin condition, the composition comprising:
(a) a first component comprising a substituted or unsubstituted diindolylmethane compound; and
(b) a second component comprising a substituted or unsubstituted retinoid compound.

20 Claims, 4 Drawing Sheets

(56) References Cited

FOREIGN PATENT DOCUMENTS

| | | |
|---|---|---|
| WO | 2010072787 A2 | 7/2010 |
| WO | 2010096868 A1 | 9/2010 |
| WO | 2011009023 A1 | 1/2011 |
| WO | 2012130698 A1 | 10/2012 |

OTHER PUBLICATIONS

U.S. Appl. No. 15/137,481 Office Action dated Feb. 13, 2017.
Search Report Under Section 17(5), Application No. GB1105050.7, Date of Search: Jul. 5, 2011.
Office Action, Chinese Patent Application No. 201280022059.X, dated Sep. 1, 2014.

* cited by examiner

COMPOSITION COMPRISING A DIINDOLYLMETHANE AND A RETINOID TO TREAT A SKIN CONDITION

CROSS-REFERENCE TO RELATED APPLICATIONS

This application is a continuation of U.S. patent application Ser. No. 16/684,300, filed on Nov. 14, 300, now U.S. Pat. No. 10,966,958, issued on Apr. 6, 2021, which is a continuation of U.S. patent application Ser. No. 15/881,453, filed on Jan. 26, 2018, now U.S. Pat. No. 10,500,189, issued on Dec. 10, 2019, which is a continuation of U.S. patent application Ser. No. 15/137,481, filed on Apr. 25, 2016, now U.S. Pat. No. 9,907,785, issued on Mar. 6, 2018, which is a continuation of U.S. patent application Ser. No. 14/864,632, filed on Sep. 24, 2015, now U.S. Pat. No. 9,351,958, issued on May 31, 2016, which is a continuation of U.S. patent application Ser. No. 14/007,247, filed on Feb. 7, 2014, now U.S. Pat. No. 9,180,117, issued on Nov. 10, 2015, which is a U.S. National Stage entry of PCT Application No: PCT/EP2012/055032 filed on Mar. 21, 2012, which claims priority to Great Britain Patent Application No. 1105050.7, filed on Mar. 25, 2011, the contents of each of which are incorporated herein by reference in their entirety.

The present application concerns a pharmaceutical composition or kit comprising a diindolylmethane (DIM) compound for use in treating a skin condition, such as acne. The composition comprises a further component in addition to the DIM in order to enhance the pharmaceutical effect of the DIM.

DIM compounds have been known for some time as pharmaceutically active agents. In particular, naturally occurring DIM has been shown to be a useful treatment for the Human Papilloma Virus (HPV). WO 03/034992 discloses the use of DIM in the treatment of verrucae and warts, conditions caused by infection with HPV. The DIM is employed either alone, or in combination with immune potentiating steroids.

DIM has also been used to treat certain other skin conditions, as well as a wide variety of other diseases. US 2005/0058600 A describes the use of DIM for the treatment of acne, alopecia, hirsuitism and even prostate cancer. It is particularly preferred that the DIM is combined with other anti-androgenics, such as bicalutamide, cyproterone, finasteride, dutasteride, ketoconazole, nilutamide, and spironolactone. The paper by Kim et al. in Molecular Carcinogenesis (vol. 49, pp. 672-683, 2010) discloses that DIM may be used to treat tumours in mice. CN 101428016 A discloses that DIM may be useful in treating acne, rheumatoid arthritis and cancer. WO 2009/103754 discloses the use of DIM to treat signs of aging. It also discloses that other additives may be employed, such as vitamin B, for improving nutrition. However, it is still necessary to improve the activity and effectiveness of DIM treatment, especially in relation to skin conditions.

DIM has also found use in combination with vitamin A in treating a number of further diseases. For example, WO 05/089412 discloses the use of DIM in combination with vitamin A for the treatment of cancer. WO 07/096886 discloses the use of DIM and vitamin A for treating eye diseases. WO 06/083458 discloses a similar combination for treating respiratory diseases. WO 06/047716 discloses another similar combination for treating human cytomegalovirus.

The present inventors have been concerned with improving the treatment of skin conditions for some time, and have taken a particular interest in acne, inflammation and signs of aging. Although DIM has found use in treating a number of conditions, as discussed above, to date its use in treating skin conditions, such as those of interest to the inventors, has not been as effective as is desired. However, in the two aspects of the invention the inventors have surprisingly discovered that DIM, when combined with certain carefully selected synergistic components, has significant efficacy in treating and preventing such skin conditions. The inventors were also concerned with reducing side effects from known treatments, and have found that the surprising combinations of each aspect of the invention have improved side effect profiles as compared with known treatments.

Accordingly, in a first aspect the present invention provides a composition for use in treating a skin condition, the composition comprising:
  (a) a first component comprising a substituted or unsubstituted diindolylmethane compound; and
  (b) a second component comprising a substituted or unsubstituted retinoid compound.

The inventors have discovered in particular that surprisingly DIM, when combined with the above selected synergistic second component, has significant efficacy in treating and preventing acne, inflammation, and/or the effects of aging in skin.

The invention further provides a pharmaceutical kit for separate, simultaneous or sequential administration for use in treating a skin condition, which kit comprises a first component and a second component, wherein the first and second components are as defined above.

The composition of the present invention, either in composition or in kit form, has been shown in clinical trials to have significant advantages over known treatments. The results of the trials will be discussed in more detail in the Examples.

The invention will now be explained in more detail by way of example only, with reference to the following Figures.

Figure 1:
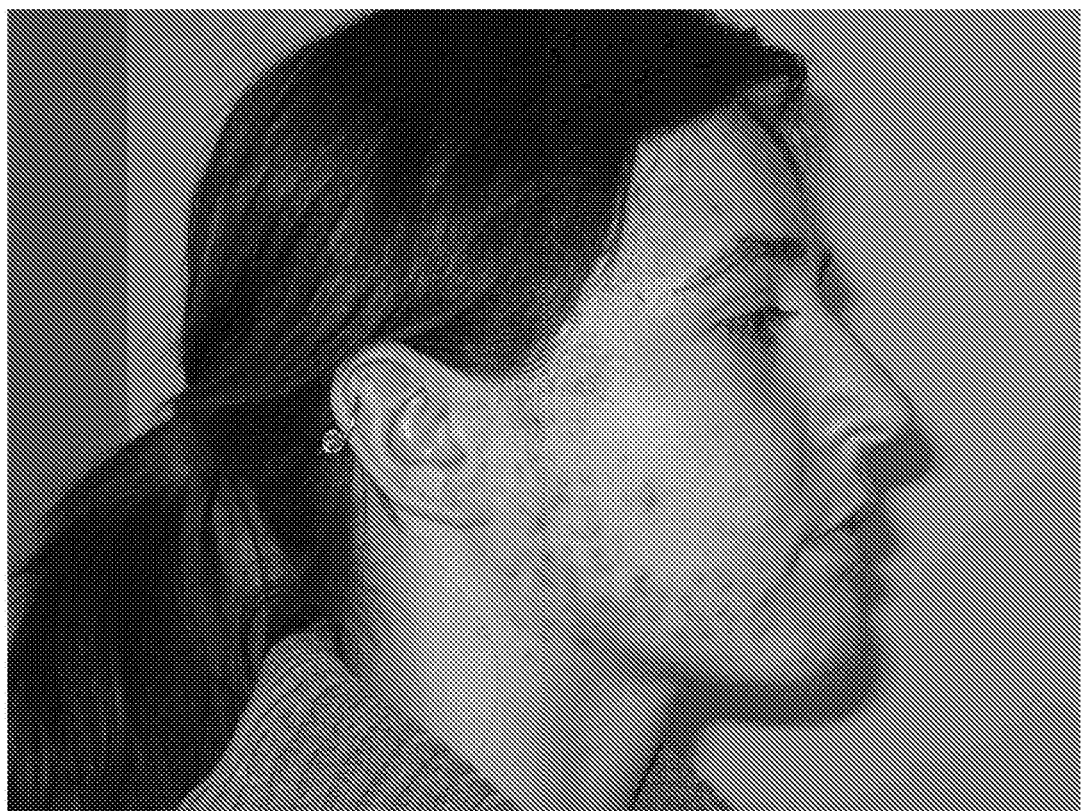
FIG. 1 shows a patient from Group A with Acne vulgaris prior to treatment with a composition of the present invention comprising BioResponse DIM and vitamin A.

The components of the composition will now be explained in further detail.

As mentioned above, the first component comprises a diindolylmethane (DIM) compound. The first component is not especially limited provided that it comprises a DIM compound, and thus may also comprise one or more further DIM compounds of the type described below.

The DIM compound may be any compound comprising a diindolylmethane group, but is preferably a compound having the following structure:

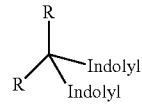

wherein the R groups may be the same or different substituents. The substituents are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

Preferably the substituents are selected from hydrogen atoms and $C_1$-$C_6$ hydrocarbon substituents such as $C_1$-$C_6$ alkyl groups (e.g. methyl, ethyl, propyl, isopropyl, and butyl groups). Most preferably both R substituents are hydrogen atoms.

The indolyl groups in the above formula are not especially limited and may be the same or different. Preferably they are both indole-3-yl groups, but alternatively both may indole-2-yl groups or one may be indole-3-yl and the other indole-2-yl. The indolyl groups may have the same or different substituents and may be unsubstituted such that all substituents are hydrogen atoms, or may be substituted with one or more of any of the substituents defined above. Preferably the substituents are selected from hydrogen atoms and $C_1$-$C_6$ hydrocarbon substituents such as $C_1$-$C_6$ alkyl groups (e.g. methyl, ethyl, propyl, isopropyl, and butyl groups). Most preferably all substituents are hydrogen atoms, i.e. the indolyl groups are unsubstituted.

Typically, but not exclusively, the first component comprises a substituted or unsubstituted 3,3'diindolylmethane compound and/or a substituted or unsubstituted 2,2'diindolylmethane compound selected from the following structures:

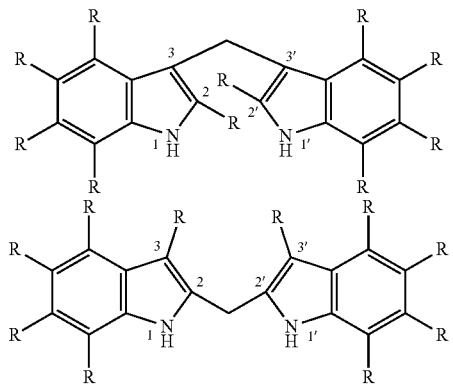

wherein the R groups may be the same or different and are selected from hydrogen atoms, or from $C_1$-$C_6$ hydrocarbon substituents.

More preferably the first component comprises a 3,3'diindolylmethane compound and/or a 2,2'diindolylmethane compound selected from the following structures:

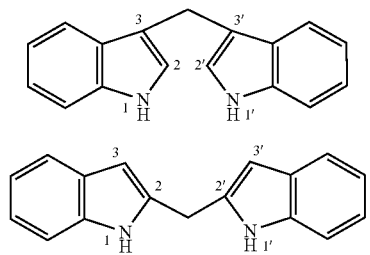

As has been mentioned above, the compositions and kits of the present invention comprise a second component comprising a substituted or unsubstituted retinoid compound. The second component typically has a beneficial effect supplementary to and/or complementary to the effect of the first component. In the present context, the effect of the second component may thus be complementary to that of the first component (i.e. its effect may differ from that of the first component, but be additionally beneficial for treatment of the skin condition in question) or may be supplementary to the effect of the first component (i.e. it may have the same effect as the first component, producing an additive effect or enhancing the pharmaceutical effect of the first component). Components that have a synergistic effect or any other beneficial relationship with the first component are thus intended to be encompassed by this definition.

The composition may also comprise one or more further components. The further components are not especially limited, and typically provide a beneficial effect as explained above. In some embodiments the further components are selected from one or more of: a further substituted or unsubstituted retinoid compound, an antibiotic compound, a substituted or unsubstituted azelaic acid compound, an oral contraceptive compound, sulphur, a sulphur-containing compound, a substituted or unsubstituted salicylic acid compound, a substituted or unsubstituted resorcinol compound, a plant product, a mineral, a vitamin (typically not vitamin A which instead may be present as a retinoid compound), and a neutraceutical product.

The further component may comprise either one such compound described above or two or more of these compounds, depending upon the requirements of the formulation.

The retinoid compound of the second component is not especially limited, and may be any such compound known in the art that is suitable for use with the skin. For example, it may be selected from a substituted or unsubstituted first generation retinoid, a substituted or unsubstituted second generation retinoid and a substituted or unsubstituted third generation retinoid. More preferably the retinoid is a substituted or unsubstituted first generation retinoid. Typically, the first generation retinoid is selected from a substituted or unsubstituted retinol, a substituted or unsubstituted retinal, a substituted or unsubstituted tretinoin (e.g. retinoic acid or Retin A), a substituted or unsubstituted isotretinoin (e.g. Accutane™), and a substituted or unsubstituted alitretinoin. Most preferably the retinoid comprises vitamin A. When the retinoid is a second generation retinoid, it is typically selected from a substituted or unsubstituted etretinate, and a substituted or unsubstituted acitretin. When the retinoid is a third generation retinoid, it is typically selected from a substituted or unsubstituted tazarotene, a substituted or unsubstituted bexarotene, and a substituted or unsubstituted adapalene.

When the further component comprises an antibiotic compound, the antibiotic compound is not especially limited, and may be any such compound known in the art that is suitable for use with the skin. Typically the antibiotic compound is suitable for oral and/ortopical application and is selected from: tetracycline, oxytetracycline, minocycline, doxycycline, erythromycin and trimethoprim.

When the further component comprises an azelaic acid compound, the azelaic acid compound is not especially limited, and may be any such compound known in the art that is suitable for use with the skin. Typically the azelaic acid compound comprises an antibacterial and/or an anti-inflammatory property.

When the further component comprises an oral contraceptive compound, the oral contraceptive compound is not especially limited, and may be any such compound known in the art that is suitable for use with the skin. Typically the oral contraceptive comprises a female hormone and/or a compound with female hormone activity, capable of counteracting the effect of a male hormone. In some embodiments, the female hormone is oestrogen and the male hormone is testosterone.

When the further component comprises sulphur, or a sulphur-containing compound, the sulphur or sulphur-containing compound is not especially limited, and may be any such compound known in the art that is suitable for use with the skin. Typically the sulphur or sulphur-containing compound comprises sulphur either alone or in combination with other substances such as alcohol, salicylic acid and/or resorcinol.

When the further component comprises a resorcinol compound, the resorcinol compound is not especially limited, and may be any such compound known in the art that is suitable for use with the skin. Typically the resorcinol compound comprises an antibacterial and/or an anti-inflammatory property.

When the further component comprises a plant product, it typically but not exclusively comprises an extract from one or more of the following:

Urtica dioica (stinging nettle)—has significant anti-inflammatory effects helping to reduce the redness and swelling in acne Ribes nigrum (blackcurrant)—has significant anti-inflammatory and antioxidant properties Echinacea purpurea and/or Echinacea augustfolia—contain active substances that enhance the activity of the immune system, reduce inflammation and antioxidant effects Cnidium monnieri—acts through its antibacterial, antifungal, and astringent properties Berberis aquafolium (Oregon grape)—may decrease sebum production, and reduce infection and inflammation Chamomile Matricaria (German chamomile)—has antibacterial properties and inactivates bacterial toxins. May reduce inflammation, and speed wound healing Phytolacca decandra (poke root)

Cruciferous vegetables—synergistic effects may be achieved by the addition of extracts, concentrates and processed extracts of cruciferous vegetables such as broccoli, sprouts etc. These may provide active products with significant added antioxidant and anti-inflammatory effects.

When the further component comprises a mineral, it typically but not exclusively comprises one or more of:

Zinc—may promote reduction of inflammation and healing of damaged skin

Chromium—may help boost the body's ability to break down glucose

Selenium—may help to balance decreased levels of antioxidant enzymes and may reduce persistent acne and help lessen the appearance of scars When the further component comprises a vitamin, it typically but not exclusively comprises one or more of:

Vitamin B complex—combinations of B vitamins B1, B2, B3, B4, B5, B6, B7, B9 and B12—may balance the metabolism of hormones, which have a significant role in the condition of Acne Vitamin C—a highly effective antioxidant, which stimulates tissue growth and repair. May contribute to the acne healing process Vitamin E—a potent antioxidant When the further component comprises a further neutraceutical product, it comprises a product that has some further nutritional or pharmaceutical property that is complementary or supplementary to the effect of the first and/or second component. Typically but not exclusively further neutraceutical products may be selected from one or more of:

Evening primrose oil—contains fatty acids, which may help decrease inflammation related to skin conditions Plant isoflavones—from foods including soy bean and red clover—have significant natural antioxidant properties and a balancing effect on estrogenic hormones Turmeric—has anti-inflammatory properties from the primary active component curcumin Omega 3 oils—long-chain n−3 fatty acids may have anti-inflammatory activity The compound of the second (and/or further) component may be substituted or unsubstituted. When the compounds are substituted, they may be substituted with any of the substituents defined above. Preferably the substituents are selected from hydrogen atoms and $C_1$-$C_6$ hydrocarbon substituents such as $C_1$-$C_6$ alkyl groups (e.g. methyl, ethyl, propyl, isopropyl, and butyl groups). Most preferably all substituents are hydrogen atoms, i.e. the compounds are unsubstituted.

A particularly advantageous embodiment of the invention is a composition or kit in which the first component comprises unsubstituted 3,3'diindolylmethane and the second component comprises a vitamin A compound (e.g. vitamin A palmitate). Further advantageous additive and excipient compounds for inclusion in such advantageous embodiments include one or more of vitamin E, vitamin C, phosphatidyl choline, microcrystalline cellulose (plant fibre), magnesium stearate and silica (further explanation on additives and excipients is provided below).

The skin condition that the present compositions and kits may be used for treating is not especially limited, but is typically selected from acne, skin inflammation and skin aging effects (such as wrinkles and other age-related blemishes). In the more preferred embodiments of the invention, the acne comprises acne vulgaris, seborrhoea, comedones, papules, pustules, nodules, cysts, boils and/or scarring.

The formulation of the composition (and the kit components) use in the present invention is not especially limited, and any formulation suitable for administration to a human or other subject may be used. However, typically the composition (and the kit components) are formulated for oral or topical administration. Thus, the composition (and the kit components) may be provided in the form of a tablet, capsule, gel, cream or ointment.

Further explanation will now be given on the bioavailability of the DIM component. Diindolylmethane (DIM) is a natural compound formed during the autolytic breakdown of glucobrassicin present in food plants of the *Brassica* genus, including broccoli, cabbage, Brussels sprouts, cauliflower and kale. The autolytic breakdown of glucobrassicin requires the catalytic reaction of the enzyme myrosinase, which is endogenous to these plants and released upon rupture of the cell wall. The compound is normally manufactured by chemical synthesis but may also be prepared by natural means from the extracts of *Brassica* vegetables, as listed above, particularly from sprouting broccoli or from broccoli seeds. As has been mentioned, any DIM compound, or combination of DIM compounds may be employed in the invention. Thus, the DIM compound may be synthetic, or may be a natural product obtained from a *Brassica* plant, as discussed above.

Typically however, the diindolylmethane compound is adapted for increased bioavailability, in order to reduce the required dosage. One such useful DIM component with increased bioavailability is BioResponse Diindolylmethane ("BioResponse DIM"; from BioResponse LLC).

The dosage of the DIM component is not especially limited, provided that it is sufficiently low to avoid toxicity, whilst still maintaining the required pharmaceutical effect. The dosage may depend on the bioavailability of the DIM, which may vary depending upon whether it is a natural or synthetic product, and on whether it has been adapted to improve bioavailability. Typically the first component is in a form suitable for providing a daily DIM dosage of 500 mg or less, preferably from 10-500 mg. Most preferably about 150 mg or about 350 mg. The higher dosages are preferred for DIM that has not been adapted to improve bioavailability. More preferably the first component is in a form suitable for providing a daily DIM dosage of 15-100 mg, preferably 18-75 mg. The lower dosages are preferred for DIM that has been adapted to improve bioavailability.

The dosage of the substituted or unsubstituted retinoid compound component is not especially limited, provided that it is sufficiently low to avoid toxicity, whilst still maintaining the required pharmaceutical effect. The dosage may depend on the bio availability of the retinoid compound, which may vary depending upon whether it is a natural or synthetic product, and on whether it has been adapted to improve bioavailability. Typically the second component is in a form suitable for providing a daily dosage of 5000 µg or less, preferably 3000 µg or less, preferably 50 µg or more, 100 µg or more, or 200 µg or more, and more preferably still from 200-3000 µg.

In the more typical embodiments, the daily dosage is provided in the form of one or more capsules or tablets, preferably in the form of 2 or 4 capsules or tablets. In these embodiments the capsules or tablets are designed to be taken during the course of a single day, such as one in the morning and one in the evening, or four spread evenly across the day, or two tablets simultaneously twice a day.

The first component and/or the second component in the compositions and kits may comprise one or more further additives, excipients and/or adjuvants. These additives, excipients and adjuvants are not especially limited, provided that they enhance the effectiveness of the first and/or second components, or are advantageous in forming a working formulation for the pharmaceutical. Diindolylmethane is a lipophilic oil-soluble compound. Similar to other oil soluble phytochemicals, the presence of oil and other lipophilic compounds, such as phosphatidylcholine and vitamin E, greatly increases the absorption and bioavailability of DIM upon oral administration. Thus, the first component typically comprises one or more further oil-soluble and/or lipophilic compounds, such as vitamin. E and/or phosphatidylcholine. Further advantageous additives may also be added to the first and/or the second component. These include, but are not limited to, microcrystalline cellulose (plant, fibre), magnesium stearate and silica.

The invention further provides a method for preparing the composition of the invention. The method is not especially limited, and any methods known in the art for blending or mixing such components may be employed, especially methods for blending and/or mixing powders. Thus, the method comprises mixing the first component with the second component to form the composition. In some embodiments, the first and second components are each, separately from each other, mixed with one or more excipients and/or additives before being mixed together to form the composition. In other embodiments, the components, additives, and/or excipients may be added sequentially to the mixture during the mixing process.

The selection of the excipients and the method of blending may be adapted in order to overcome any mixing, flow and fill issues or punch issues with the composition. The BioResponse DIM is provided in micro-encapsulated form, such that the powder particles have a tendency to clump together. In such circumstances the blending method is adapted to avoid creating hot spots of increased concentrations of the active ingredients. In addition, the composition is hydroscopic and light sensitive such that processing/blending times should be kept to a minimum, and in storage the powder should be protected from both light and air.

As additives and excipients, microcrystalline cellulose, magnesium silicate, tricalcium phosphate and magnesium stearate (a traditional lubricant) are preferred to help with flow characteristics and/or lubrication. However, other additives and excipients known in the art may be employed if desired. In some embodiments, it is desirable that the composition comprises 55-60% by weight of tricalcium phosphate.

The correct blending of all ingredients is important in achieving uniform capsule fills of the active ingredient. A V-blender is highly effective for successful mixing. Preferably, a minimum 316 grade stainless steel vessel is used for this process. Sieving is preferred at one or more of the start, the middle, and the end of the process. Blend studies to confirm blend uniformity should be completed to validate the method and formulation. Such methods and techniques are known in the art.

The invention also provides a second aspect, which comprises a composition for use in treating a skin condition, the composition comprising:
 (a) a first component comprising a substituted or unsubstituted diindolylmethane compound; and
 (b) a second component different from the first component, wherein the second component has a beneficial effect supplementary to and/or complementary to the effect of the first component, wherein the second component is selected from an antibiotic compound, a substituted or unsubstituted azelaic acid compound, an oral contraceptive compound, sulphur, sulphur-containing compound, a substituted or unsubstituted salicylic acid compound, a substituted or unsubstituted resorcinol compound, a plant product, a mineral, a vitamin, and a neutraceutical product.

In this second aspect, the antibiotic compound, substituted or unsubstituted azelaic acid compound, oral contraceptive compound, sulphur, sulphur-containing compound, substituted or unsubstituted salicylic acid compound, substituted or unsubstituted resorcinol compound, plant product, mineral, vitamin, and neutraceutical product may be any such compound or product as already described above in relation to the further component used in the first aspect of the invention. Accordingly, in the second aspect of the invention, the second component is not a retinoid compound, but is selected from the above compounds instead.

Any of the preferred features set out in the claims and description in relation to the first aspect of the invention may also apply to the second aspect of the invention. The methods, uses and kits of the first aspect are also applicable to the second aspect.

The invention will now be described in further detail by way of example only, with reference to the following specific embodiments.

EXAMPLES

Manufacture of Composition

Two different batches of DIM and vitamin A formulation were manufactured. The details of manufacture and formulation are set out below.

Formulation 1

1 capsule contains:
 75 mg BioResponse DIM (BioResponse LLC)
 200 μg vitamin A palmitate retinol equivalents (366.4 μg retinyl palmitate). This is equivalent to 2.666 mg of 250,000 IU/g vitamin A palmitate (BASF)
 175 mg tricalcium phosphate
 20 mg microcrystalline cellulose
 10 mg vitamin C (ascorbic acid)
 10 mg fumed silicon dioxide (or a fine particle precipitated silica)
 6 mg magnesium stearate Blending Method or Formulation 1

Mixing was carried out in a sequential process according to the following protocol:
 1. The BioResponse DIM was sieved through a fine sieve and then mixed with the magnesium stearate, half of the tricalcium phosphate and the silicon dioxide for 10 mins in a V mixer. The mixed powder was transferred into a food grade bag.
 2. Separately, the vitamin C and retinyl palmitate were mixed with the second half of the tricalcium phosphate and the microcrystalline cellulose for 10 mins in a V mixer.
 3. The mixed powders obtained from 1 and 2 were blended together for 20 mins in a V mixer, then sieved, and mixed further for 1 hour and 10 minutes in a V mixer.
 4. The blended powder was transferred to a suitable opaque and air-tight container to ensure minimal contact with light and oxygen.
 5. A sample was taken from the top and bottom of the batch to test for uniformity of mixing.

Formulation 2

1 capsule (297 mg) contains:
 75 mg BioResponse DIM (BioResponse LLC)
 200 μg vitamin A palmitate retinol equivalents (366.4 μg retinyl palmitate). This is equivalent to 1.333 mg of 500,000 IU/g vitamin A palmitate (BASF)
 175 mg tricalcium phosphate
 20 mg cellulose fibre
 10 mg vitamin C (ascorbic acid)
 10 mg silicon dioxide (Neosyl)
 6 mg magnesium stearate Blending Method for Formulation 2
 1 The BioResponse DIM was sieved thoroughly through a fine mesh into a clean, sterile, plastic bag. The sieved BioResponse DIM, the vitamin C, and the retinyl palmitate were pre-mixed with the silicon dioxide first in the sealed plastic bag for 5 minutes.
 2. The tricalcium phosphate and microcrystalline cellulose were then added to the premix and thoroughly mix for an additional 5 minutes. The resulting mixture was added to a V mixer and mixed for 10 minutes.
 3. The magnesium stearate was then added, and powder was mixed for an additional 10 minutes.
 4. the resulting mixed powder was removed and passed through a fine grade sieve. It was then transferred back into the V mixer and mixed for 30 minutes.
 5. The resulting mixture was transferred to a suitable opaque and air-tight container to ensure minimal contact with light and oxygen.
 6. A sample was taken from the top, centre, and bottom of the batch to test for uniformity of mixing.

Encapsulation

The formulations referred to above may be encapsulated. The DIM is spray dried into particles of approximately 8 to 12 microns in diameter. The powder flow properties of particles at this size are very challenging. The powder, because of the specific ingredients that are used to achieve the bioavailability requirements, are somewhat cohesive. Because of this, certain types of encapsulation equipment can have difficulty with continued operation without stopping to clean punch faces or to adjust fill volumes.

DIM is known to be light sensitive. Therefore, opaque capsules are preferred, typically, size "0" capsules. Light resistant containers are preferred.

Patient Testing

The aim of this survey was to ascertain the efficacy of using oral DIM together with Vitamin A in order to treat Grade II to IV active acne. The results showed impressive improvements in the condition over a 3 month period with no side effects or worsening of the condition.

The survey was conducted using 2 trial groups, Group A and Group B. The composition employed comprised Bio-Response DIM (75 mg per capsule) together with Solgar vitamin A (retinyl palmitate) (5,000 IU per tablet).

Group A took between 150 mg and 300 mg BioResponse DIM together with between 5,000 IU and 10,000 IU vitamin A daily. The results were measured using:

Visia skin analysis equipment
Photographs
1.—Self-reporting: Group A rated their acne on a scale of 1 to 10 with 1 being good and 10 being bad before starting the supplements and then again at the end of three months. The results (marks out of 10 in percent) are shown in Table 1.

Group B took 300 mg BioResponse DIM together with 2,500 IU Vitamin A daily. The results were measured using:

Visia skin analysis equipment
Photographs
Self-reporting: At the beginning of the trial, the subjects rated their acne on a scale of 1 to 10 with 1 being good and 10 being bad. Subsequently they were asked to rate their skin again after 1, 2 and 3 months (end of the trial). A different rating scale was used. This time the subjects were asked to rate their acne on a scale between 1 and 6 with 1 being the best their skin has been and 6 being the worst. The results (marks out of 10, or out of 6 in percent) are shown in Table 2.

Results

TABLE 1

| Group A self-scoring | | | | | | | | | | | |
|---|---|---|---|---|---|---|---|---|---|---|---|
| Patient No. | 1 | 2 | 3 | 4 | 5 | 6 | 7 | 8 | 9 | 10 | 11 |
| Before (%) | 100 | 70 | 60 | 80 | 70 | 60 | 70 | 60 | 30 | 50 | 90 |
| After (%) | 30 | 40 | 24 | 35 | 10 | 40 | 70 | 40 | 10 | 0 | 20 |

Figure 2:
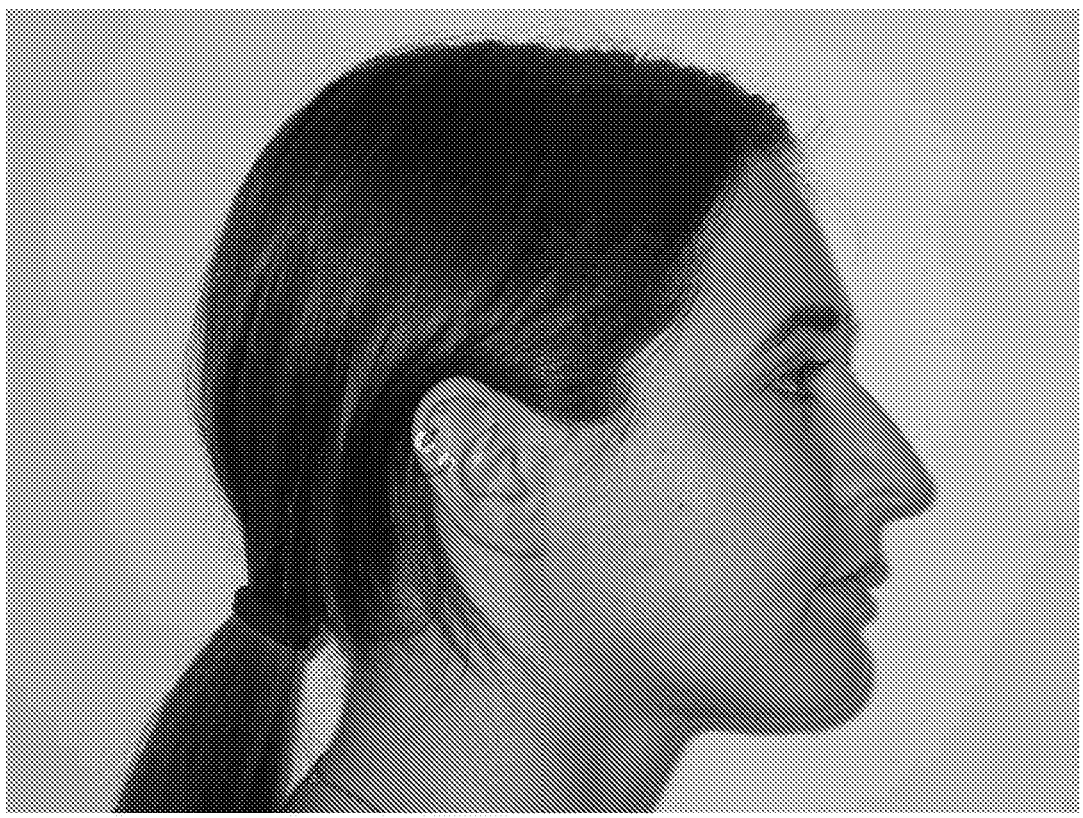
FIG. 2 shows the patient from FIG. 1 after treatment with a composition of the present invention comprising BioResponse DIM and vitamin A.

The average score for Group A before treatment was 67%, whilst the average score after treatment was 29%, indicating a very large improvement. The photographs showing before and after conditions for patient 12 of group A are shown in FIG. 1 and FIG. 2 respectively.

TABLE 2

| Group B self-scoring | | | | | | | | | | | | |
|---|---|---|---|---|---|---|---|---|---|---|---|---|
| Patient No. | 1 | 2 | 3 | 4 | 5 | 6 | 7 | 8 | 9 | 10 | 11 | 12 |
| Before | 50 | 60 | 100 | 70 | 50 | 90 | 60 | 50 | 80 | 70 | 70 | 80 |
| After 3 m (%) | 50 | 50 | 17 | 83 | 33 | 50 | 17 | 33 | 83 | 83 | 17 | 33 |

Figure 3:
FIG. 3 shows a patient from Group B with Acne vulgaris prior to treatment with a composition of the present invention comprising BioResponse DIM and vitamin A.
Figure 4:
FIG. 4 shows the patient from FIG. 3 after treatment with a composition of the present invention comprising BioResponse DIM and vitamin A.

The average score for Group B before treatment was 69%, whilst the average score after treatment was 46%, again indicating a very large improvement. The photographs showing before and after conditions for patient 11 of group B are shown in FIG. 3 and FIG. 4 respectively.

The results show that of the 23 patients who completed the study, 18 showed improvement in their condition (patients A7, B1, B4, B9, B10 showed no significant change in the condition). The average across the 18 was a 41% reduction, which represents a 59% improvement on the original score.

Evidence of the typical reduction in acne shown by patients treated with the agent of the invention is provided in FIGS. 1-4 in the form of 'before and after' photographs. The significant improvement is clearly visible.

These results demonstrate the significant potential of the proposed combined formulation in the treatment of acne and associated conditions, especially when DIM having improved bioavailability (as compared with pure DIM) is employed.

The invention claimed is:

1. A composition in dosage form for use in treating a skin condition, the composition, comprising:
    (a) a first component comprising a substituted or unsubstituted 3,3' diindolylmethane compound or a substituted or unsubstituted 2,2' diindolylmethane compound having a structure of:

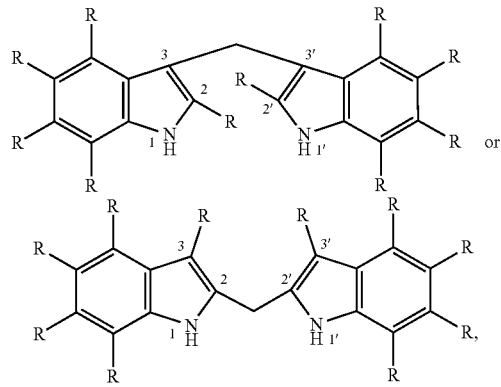

wherein each R is independently selected from selected from hydrogen and $C_1$-$C_6$ hydrocarbon substituents; and
    (b) a second component comprising a substituted or unsubstituted retinoid compound selected from a substituted or unsubstituted retinal, a substituted or unsubstituted retinol, a substituted or unsubstituted tretinoin, a substituted or unsubstituted isoretinoin, and a substituted or unsubstituted alitretinoin.

2. The composition of claim 1, wherein the composition comprises a further component selected from one or more of: a further substituted or unsubstituted retinoid compound, an antibiotic compound, a substituted or unsubstituted azelaic acid compound, an oral contraceptive compound, sulphur, a sulphur-containing compound, a substituted or unsubstituted salicylic acid compound, a substituted or unsubstituted resorcinol compound, a plant product, a mineral, a vitamin, and a neutraceutical product.

3. The composition of claim 1, wherein the retinoid is selected from a substituted or unsubstituted retinal, a substituted or unsubstituted retinal, a substituted or unsubstituted tretinoin (retinoic acid or Retin A), a substituted or unsubstituted isoretinoin, and a substituted or unsubstituted alitretinoin.

4. The composition of claim 3, wherein the retinoid comprises vitamin A.

5. The composition of claim 1, wherein the ratio (mg:μg) of the first and the second component is between 10:3000 and 500:200.

6. The composition of claim 5, wherein the first component is in non-microencapsulated form.

7. The composition of claim 6, wherein the ratio (mg:µg) of the first and the second component is between 150:3000 and 350:200.

8. The composition of claim 7, wherein the first component is in microencapsulated form.

9. The composition of claim 8, wherein the ratio (mg:µg) of the first and the second component is between 15:3000 and 100:200.

10. The composition of claim 8, wherein the ratio (mg:µg) of the first and the second component is between 18:3000 and 75:20.

11. The composition of claim 1, wherein the first and the second components are provided in a single formulation.

12. The composition of claim 1, wherein the first and the second components are provided in separate formulations.

13. The composition of claim 1, wherein the first component comprises an unsubstituted diindolylmethane compound, and wherein the second component comprises vitamin A.

14. The composition of claim 13, wherein the unsubstituted diindolylmethane compound is 3,3'-diindolylmethane.

15. The composition of claim 14, wherein the 3,3'-diindolylmethane is in microencapsulated form for improved bioavailability.

16. The composition of claim 13, wherein the second component comprises retinyl palmitate.

17. The composition of claim 1, wherein the skin condition is selected from acne, inflammation, and aging.

18. The composition of claim 17, wherein the acne comprises acne vulgaris, seborrhoea, comedones, papules, pustules, nodules, cysts, boils and/or scarring.

19. The composition of claim 1, wherein the first and the second components are provided in a single formulation suitable for oral administration.

20. The composition of claim 1, wherein the composition further comprises at least one of an excipient and adjuvant.

* * * * *